US008574619B2

(12) United States Patent
Lines

(10) Patent No.: US 8,574,619 B2
(45) Date of Patent: Nov. 5, 2013

(54) REDUCING CHOLESTEROL LEVELS WITH COMBINED USE OF QUERCETIN AND STATIN

(75) Inventor: Thomas Christian Lines, Grand Duchy of Luxembourg (LU)

(73) Assignee: Quercegen Pharmaceuticals, LLC, Marlborough, MA (US)

( * ) Notice: Subject to any disclaimer, the term of this patent is extended or adjusted under 35 U.S.C. 154(b) by 999 days.

(21) Appl. No.: 12/205,070

(22) Filed: Sep. 5, 2008

(65) Prior Publication Data

US 2010/0061968 A1    Mar. 11, 2010

(51) Int. Cl.
A61K 47/00    (2006.01)

(52) U.S. Cl.
USPC ......... 424/439; 424/93.51; 514/7.4; 514/356; 514/474; 514/728; 514/731

(58) Field of Classification Search
None
See application file for complete search history.

(56) References Cited

U.S. PATENT DOCUMENTS

| | | | |
|---|---|---|---|
| 5,026,721 A | 6/1991 | Dudrick et al. | |
| 5,804,594 A | 9/1998 | Murad | |
| 5,846,569 A | 12/1998 | Anderson et al. | |
| 6,103,756 A | 8/2000 | Gorsek | |
| 6,121,249 A * | 9/2000 | Weissman et al. | 514/52 |
| 6,203,818 B1 * | 3/2001 | Vester | 424/569 |
| 6,210,701 B1 | 4/2001 | Darland et al. | |
| 6,261,589 B1 | 7/2001 | Pearson et al. | |
| 6,277,426 B1 | 8/2001 | Reust | |
| 6,277,427 B1 | 8/2001 | Husz | |
| 6,299,925 B1 | 10/2001 | Xiong et al. | |
| 6,352,712 B1 | 3/2002 | Lukaczer et al. | |
| 6,491,948 B1 | 12/2002 | Buchholz et al. | |
| 6,511,675 B2 | 1/2003 | Siddiqui et al. | |
| 6,551,629 B1 | 4/2003 | Gorsek | |
| 6,579,544 B1 | 6/2003 | Rosenberg et al. | |
| 6,821,536 B2 | 11/2004 | Lines et al. | |
| 7,041,652 B1 | 5/2006 | Buchholz et al. | |
| 7,270,840 B2 | 9/2007 | Lines et al. | |
| 2002/0025350 A1 | 2/2002 | Siddiqui et al. | |
| 2002/0151599 A1 | 10/2002 | Buchholz et al. | |
| 2003/0054357 A1 | 3/2003 | Young et al. | |
| 2003/0068391 A1 | 4/2003 | Harris et al. | |
| 2004/0126461 A1 | 7/2004 | Lines et al. | |
| 2005/0031737 A1 | 2/2005 | Lines et al. | |
| 2005/0266121 A1 | 12/2005 | Lines et al. | |
| 2007/0148210 A1 | 6/2007 | Lines et al. | |
| 2008/0015247 A1 | 1/2008 | Lines | |
| 2008/0032987 A1 | 2/2008 | Lines | |
| 2009/0148433 A1 * | 6/2009 | Naidu et al. | 424/94.61 |

FOREIGN PATENT DOCUMENTS

| | | |
|---|---|---|
| WO | WO 98/41195 | 9/1998 |
| WO | WO 00/12085 | 3/2000 |
| WO | WO 02/07768 | 1/2002 |
| WO | WO2004/037015 | 5/2004 |
| WO | WO 2008/011363 | 1/2008 |

OTHER PUBLICATIONS

Shepherd et al., Am J Cardiol., 2003, vol. 91, Issue 5, Abstract.*
Zern et al., J. Nutr., 2003, vol. 133, p. 2268-2272.*
Do et al., Biochemical and Biophysical Research Communications, vol. 2008, p. 55-59.*
Bors et al., "Flavanoids and Polyphenols: Chemistry and Biology," *Handbook of Antioxidants*, pp. 409-416 (1996).
Hye Syn Gwak, et al. "Solubility and physicochemical stability of quercetin in various vehicles" Journal of Korean Pharmaceutical Science, 2004, 34(1), pp. 29-34.
Chow et al., "Phase I Pharmacokinetic Study of Tea Polyphenols Following Single-dose Administration of Epigallocatechin Gallate and Polyphenon E," Cancer Epidemiology, Biomarkers & Prevention 10:53-58 (2001) XP-002366662.
Crespy et al., "Quercetin, but not Its Glycosides, Is Absorbed from the Rat Stomach," Journal of Agricultural and Food Chemistry, vol. 50, pp. 68-621 (2002).
Dequan et al., "Survey of Bioflavonoids," Food and Fermentation Industries, 25(16): 52-56 (1999) (Translation of English Abstract).
Erlund et al., "Pharmacokinetics of Quercetin from Quercetin Aglycone and Rutin in Healthy Volunteers," Eur. J. Clin. Pharmacol., 56:545-553 (2000).
Guardia et al., "Anti-Inflammatory Properties of Plant Flavinoids. Effect of Rutin, Quercetin and Hesperidin on Adjuvant Arthritis in Rat," II Farmaco, 56: 683-687 (2001).
Koo et al., "Pharmacological Effects of Green Tea on the Gastrointestinal System," European Journal of Pharmacology 500:177-184 (2004).
Min et al., "The Chemistry and Medical Application of Tea Polyphenol," Hubei Chemical Industry, 2001, 3, 29-31 (Translation of English Abstract).
Saucier et al., "Synergetic Activity of Catechin and Other Antioxidants," Journal of Agricultural and Food Chemistry, 47(11): 4491-4494 (1999).
Sesink et al., "Quercetin Glucuronides but Not Glucosides Are Present in Human Plasma After Consumption of Quercetin-3-Glucoside or Quercetin-4-Glucoside," Human Nutrition and Metabolism Research Communication, pp. 1938-1941 (2001).
Thomas et al., "Ascorbate and Phenolic Antioxidant Interations in Prevention of Liposomal Oxidation," Lipids 27(7) (1992).

(Continued)

*Primary Examiner* — Kade Ariani
(74) *Attorney, Agent, or Firm* — Cesari and McKenna, LLP

(57) ABSTRACT

A method of reducing the cholesterol level of a subject by administering to that subject quercetin, vitamin C, vitamin B3, and statin.

37 Claims, No Drawings

(56) References Cited

OTHER PUBLICATIONS

Walle et al., "Quercetin Glucosides Are Completely Hydrolyzed in Ileostomy Patients before Absorption," Human Nutrition and Metabolism Research Communication, pp. 2658-2661 (2000).

Mashkovsky, M.D., Drugs, Manual for Physicians, vol. 2, 14th Edition, revised corrected and supplemented Moscow, 2001; pp. 84-88 [English translation provided].

Belenkow, Yu N., Cardiology National Guidelines, pp. 474-481 Moscow 2007 [English translation provided].

Broncel et al., "The Comparison in vitro the effects of pravastatin and quercetin on the selected structural parameters of membrane erythrocytes from patients with hypercholesterolemia," Pol. Merkur Lekarski, 22(128):112-116 (2007) [English Abstract].

Lazar et al. "Beneficial effects of combined treatment statins-antioxidant agents in patients with multiple coronary risk factors—Epidemiological study," Atherosclerosis, 151 (1): 107 (2000) XP027334008.

Omoigui Sota, "The Interleukin-6 inflammation pathway from cholesterol to aging—Role of statins, bisphosphonates and plant polyphenols in aging and age-related diseases," Immunity and Aging, 4(1), p. 1 (2007) XP021025325 Abstract.

Naruszewicz et al., "Combination therapy of statin with flavonoids rich extract from chokeberry fruits enhanced reduction in cardiovascular risk markers in patients after myocardial infraction (MI)" Atherosclerosis, 194(2): e179-e184 (2007) XP022288431.

Jenkins et al., "Direct Comparison of Dietary Portfolio vs Statin on C-Reactive Protein," European Journal of Clinical Nutrition, 59(7): 851-861 (2005) XP009082376.

* cited by examiner

REDUCING CHOLESTEROL LEVELS WITH COMBINED USE OF QUERCETIN AND STATIN

BACKGROUND

Quercetin, a natural antioxidant, inhibits both acute and chronic phases of free-radical induced diseases. It also acts synergistically with other natural antioxidants in their reactions with biologically relevant oxygen species, e.g., hydroxyl radicals, superoxides, oxysulfurs, sulfur dioxide, and nitrogen dioxide.

Statins are a class of hypolipidemic drugs that inhibit HMG-CoA reductase, a rate-limiting enzyme in cholesterol synthesis.

SUMMARY

The present invention is based on the unexpected discovery that a statin and a composition containing quercetin, vitamin B3, and vitamin C, in combination, significantly reduces the plasma cholesterol level in a patient.

Accordingly, this invention features a method of reducing the plasma cholesterol level in a patient with (a) a first composition containing quercetin, vitamin C, vitamin B3, and optionally, folic acid, and (b) a second composition containing a statin and optionally one or more of ezetimibe, colesevelam, fenofibrate, red rice yeast, omega-3, and niacin. In one example, the second composition contains Vytorin (i.e., a combination of simvastatin and ezetimibe).

In the first composition, the weight ratio between quercetin, vitamin C, and vitamin B3 can be 1:0.2-2.5:0.02-1, e.g., 1:0.5-1:0.02-0.2, 1:0.5-1:0.25-1, or 1:1:0.04. When it contains folic acid, the weight ratio between quercetin, vitamin C, vitamin B3, and folic acid can be 1:0.2-2.5:0.02-1:0.2-2 (mg/mg/mg/mcg), e.g., 1:0.5-1:0.02-0.2:0.5-1 (mg/mg/mg/mcg), 1:0.5-1:0.25-1:0.5-1 (mg/mg/mg/mcg), or 1:1:0.04:0.8 (mg/mg/mg/mcg). The unit "mcg" is an abbreviation of microgram.

The first composition, either in dry form (e.g., powder or tablet) or in liquid form (e.g., beverage or syrup), can be a dietary supplement in the form of a tablet, a capsule, a soft chew, or a gel. It can contain various inactive additives (e.g., excipients, sweeteners, and artificial flavors). The composition can also be a food product. Examples include tea (e.g., a tea drink and the contents of a tea bag), soft drinks, juice (e.g., a fruit extract and a juice drink), milk, coffee, jelly, ice cream, yogurt, cookies, cereals, chocolates, and snack bars.

Both the first and second compositions can be pharmaceutical formulations containing one or more pharmaceutically acceptable carriers. The pharmaceutical formulations can be in the form of a liquid, a powder, a tablet, a capsule, a soft chew, or a gel.

To practice the method of this invention, a subject is administered with an effective amount of the first composition and an effective amount of the second composition. The subject can be a patient suffering from or at risk for developing a higher plasma cholesterol level relative to a healthy subject.

An effective amount of the first composition can be an amount that provides 250 mg-2000 mg quercetin per day (e.g., 500 mg, 1000 mg, 1500 mg, or 2000 mg). In one example, the effective amount of the first composition is an amount that provides per day 500 mg-1000 mg quercetin, 500-1000 mg vitamin C, 20-40 mg vitamin B3, and 400-800 mcg folic acid, e.g., 500 mg quercetin, 500 mg vitamin C, 20 mg vitamin B3, and 400 mcg folic acid per day, or 1000 mg quercetin, 1000 mg vitamin C, 40 mg vitamin B3, and 800 mcg folic acid per day.

An effective amount of the second composition can be an amount that provides per day 10-20 mg atrovastatin, 10-80 mg vytorin, 40 mg provastatin and 145 tricor, or 10-40 mg vytorin and 1000 mg niacin.

Also within the scope of this invention is the use of the first and second compositions described above for reducing the cholesterol level in a subject or for the manufacture of a medicament(s) for reducing cholesterol levels.

The details of one or more embodiments of the invention are set forth in the description below. Other features, objects, and advantages of the invention will be apparent from the description and from the claims.

DETAILED DESCRIPTION

Described herein is a method of reducing the cholesterol level in a patient with an effective amount of a first composition containing quercetin, vitamin C, vitamin B3, and optionally folic acid, and an effective amount of the second composition containing a statin. The term "effective amount," as used herein, refers to the amount of each active agent which, upon administration with one or more other active agents to a subject in need thereof, is required to confer therapeutic effect on the subject. Effective amounts vary, as recognized by those skilled in the art, depending on route of administration, excipient usage, and co-usage with other active agents.

It is known that, upon oral administration, a combination of quercetin, vitamin B3, and vitamin C results in a significantly higher quercetin concentration in plasma than quercetin alone. More specifically, a combination of quercetin, vitamin B3, and vitamin C maintains quercetin levels in plasma up to five times those of quercetin alone or a combination of quercetin and vitamin B3; and that a combination of quercetin, vitamin B3, and vitamin C results in a quercetin half life in plasma twice as long as that of quercetin alone and about one and a half times that of a combination of quercetin and vitamin B3. See US 20080015247 and US20080032987.

In the first composition, the weight ratio between quercetin, vitamin C, vitamin B3, and folic acid composition used in the method of this invention can be 1:0.2-2.5:0.02-1:0.2-2 (mg/mg/mg/mcg), or any ratio in between. For example, the weight ratio can be 1:0.5-1:0.25-1:0.5-1 (mg/mg/mg/mcg), or 1:1:0.04:0.8 (mg/mg/mg/mcg). Preferably, a subject is administered, once or periodically per day, with the composition in an amount that provides 250 mg to 2000 mg (e.g., 250-500 mg, 500-1000 mg, 1000-1500 mg, or 1500-2000 mg) of quercetin, which can be quercetin aglycon, isoquercetin, or a combination thereof. In one example, the effective amount of the first composition is an amount that provides per day 250-2000 mg quercetin (e.g., 250-500 mg, 500-1000 mg, 1000-1500 mg, or 1500-2000 mg), 250-2000 mg vitamin C (e.g., 250-500 mg, 500-1000 mg, 1000-1500 mg, or 1500-2000 mg), 20-60 mg (e.g., 20-40 mg) vitamin B, and 200-1000 mcg (e.g., 400-800 mcg) folic acid. In another example, the amount of vitamin B is 250-2000 mg.

The term "quercetin" refers to quercetin aglycon, a quercetin derivative, or a mixture thereof. Quercetin derivatives include, but are not limited to quercetin-3-O-glucoside (also known as isoquercetin), quercetin-5-O-glucoside, quercetin-7-O-glucoside, quercetin-9-O-glucoside, quercetin-3-O-rutinoside, quercetin-3-O-[α-rhamnosyl-(1→2)-α-rhamnosyl-(1→6)]-β-glucoside, quercetin-3-O-galactoside, quercetin-7-O-galactoside, quercetin-3-O-rhamnoside, and quercetin-7-O-galactoside. After digestion, quercetin derivatives are converted to quercetin aglycon and other active derivatives, which are absorbed in the body. The quantity of quercetin mentioned above refers to that of quercetin aglycon or the quercetin moiety of a quercetin derivative. Quercetin can be added to the composition either in a pure form or as an ingredient in a mixture (e.g., a plant extract). Examples of commercially available quercetin include QU995 (containing 99.5% quercetin) and QU985 (containing 98.5% quercetin) from Quercegen Pharma LLC (Newton, Mass.) and Merck KGaA (Brazil).

"Vitamin B3" mentioned herein includes vitamin B3 in its various forms, including niacinamide, nicotinic acid, nicotinamide, inositol hexaniacinate.

"Vitamin C" mentioned herein includes vitamin C (i.e., L-ascorbic acid, D-ascorbic acid, or both) and its salts (e.g., sodium ascorbate).

"Folic acid" mentioned herein includes vitamin B9, folate, pteroylglutamic acid, and their derivatives, e.g., methylfolate.

The first composition can include quercetin, vitamin C, vitamin B3, and folic acid as the only active ingredients. It also can further contain one or more other active ingredients, such as isoflavone (e.g., genistein or genistin), curcumin, resveratrol, isoquercetin, luteolin, epigallocatechin gallate (EGCG), CoQ10, EPA, and DHA. These active ingredients can be added to the composition either in a pure form or as a component in a mixture (e.g., an extract from a plant or an animal). A suitable daily dosage of each of these ingredients can vary depending on, for example, the disorder or condition to be treated and the physical states of the subjects. Exemplary daily dosages of some of these ingredients are: 20-2,500 mg (preferably 250-1,000 mg) of curcumin, 10-1,000 mg (preferably 100-500 mg) of resveratrol, 10-1,000 mg (preferably 100-250 mg) of isoquercetin, 50-1,000 mg (preferably 100-700 mg) of EGCG, 25-300 mg (preferably 50-100 mg) of genistin/genistein, 10-1,000 mg (preferably 100-200 mg) of luteolin, 50-1,000 mg (preferably 70-500 mg) of EPA, and 50-1,000 mg (preferably 80-700 mg) of DHA. Further, it can be sweetened, if necessary, by adding a sweetener such as sorbitol, maltitol, hydrogenated glucose syrup and hydrogenated starch hydrolyzate, high fructose corn syrup, cane sugar, beet sugar, pectin, and sucralose. The composition can also contain amino acids, fatty acids, proteins, fibers, minerals, a flavor enhancer, or a coloring agent. Exemplary amino acids include theanine (e.g., L-theanine) and alanine (e.g., L-alanine). Exemplary fatty acids include omega-3 fatty acids (e.g., linolenic acid), omega-6 fatty acids (e.g., linoleic acid), and omega-9 fatty acids (e.g., oleic acid). Exemplary proteins include plant proteins, such as soy proteins and chia seed proteins. Exemplary fibers include plant fibers, such as soy fibers and chia seed fibers. These ingredients can be added in the above-described composition either in a pure form or as a component in a mixture (e.g., an extract from a plant or an animal).

When any of the first compositions described above are in powder form, it can be used conveniently to prepare beverage, paste, jelly, capsules, or tablets. Lactose and corn starch are commonly used as diluents for capsules and as carriers for tablets. Lubricating agents, such as magnesium stearate, are typically included in tablets.

If desired, the second composition used in the method of this invention contains a statin as the only active ingredient, or only the statin. Optionally, it can contain another component that promotes statin activity. Exemplary statins include but are not limited to atorvastatin (e.g., Lipitor), cerivastatin, fluvastatin (e.g., Lescol), mevastatin, pitavastatin, lovastatin (e.g., Mevacor or Altocor), provastatin (e.g., Pravachol or Selektine), rosuvastatin (e.g., Crestor), and simvastatin (e.g., Zocor). The component that promotes statin activity can be a statin stablizer (e.g., Welchol), a fenofibrate (e.g., Tricor), fish oil (e.g., omega-3), a bile acid sequestrant (e.g., colesevelam), red yeast, Zetia, niacin (e.g., nicotinic acid), or niaspan. Omega-3 can be eicosapentaenoic acid (EPA), docosahexaenoic acid (DHA), or a combination thereof.

The first and second compositions used to practice the method of this invention can be in various forms. For example, the first composition can be a soft chew composition that includes quercetin, niacinamide, ascorbic acid, sodium ascorbate, sugar, corn syrup, sucralose, soy lecithin, corn starch, glycerin, palm oil, xylitol, carrageenan, FD&C Yellow #6, FD&C Yellow #5, and natural and/or artificial flavors. An exemplary serving of this soft chew composition includes 250 mg quercetin, 250 mg vitamin C, 10 mg vitamin B3 (e.g., niacinamide), and 200 mcg folic acid. In another example, one serving of this soft chew composition contains 125 mg quercetin, 125 mg vitamin C, 5 mg vitamin B3, and 100 mcg folic acid. A subject can take one to eight servings (e.g., 4 servings) of this soft chew composition daily. The amounts taken can vary depending on, for example, the disorder or condition to be treated and the physical states of the subject.

Each of the first and second compositions used to practice the method of this invention can be a dietary supplement or a pharmaceutical formulation. As a dietary supplement, additional nutrients, such as minerals or amino acids may be included. The composition can also be a food product. As used herein, the term "food" broadly refers to any kinds of liquid and solid/semi-solid materials that are used for nourishing humans and animals, for sustaining normal or accelerated growth, or for maintaining stamina or alertness. Examples of human food products include, but are not limited to, tea-based beverages, juice, coffee, milk, jelly, cookies, cereals, chocolates, snack bars, herbal extracts, dairy products (e.g., ice cream, and yogurt), soy bean product (e.g., tofu), and rice products.

Alternatively, the compositions can be a pharmaceutical composition containing a pharmaceutically acceptable carrier, i.e., a carrier that it is compatible with the active ingredient of the composition, and preferably, capable of stabilizing the active ingredient and not deleterious to the subject to be treated.

The first composition and the second composition can be formulated separately, or combined together to form a single medicament.

In the method of this invention, an effective amount of each of the first and second compositions is delivered, either combined or separately, to a subject via a conventional route of administration to improve his or her renal function. The term "administration" covers oral or parenteral delivery to a subject a composition of the invention in any suitable form, e.g., food product, beverage, tablet, capsule, suspension, and solution. The term "parenteral" refers to subcutaneous, intracutaneous, intravenous, intramuscular, intraarticular, intraarterial, intrasynovial, intrasternal, intrathecal, intralesional, and intracranial injection, as well as various infusion techniques.

The compositions described above can be preliminarily screened for their efficacy in treating the above-described conditions by in vitro assays and then confirmed by animal experiments and clinic trials. Other suitable analytical and biological assays are apparent to those of ordinary skill in the art. For example, the bioavailability of quercetin can be measured by conducting pharmacokinetic studies and evaluated by the area under the curve in a plasma-drug concentration time curve.

Without further elaboration, it is believed that one skilled in the art can, based on the above description, utilize the present invention to its fullest extent. The following specific embodiment is, therefore, to be construed as merely illustrative, and not limitative of the remainder of the disclosure in any way whatsoever. All publications cited herein are incorporated by reference.

Reducing Serum Cholesterol Levels in Patients with Statin and a Soft Chew Containing Quercetin, Vitamin C, Vitamin B3, and Folic Acid 181 patients, all over the age of 50, were recruited for this study. About 12% of the patients were under treatment of statin, e.g., Lipitor, Vytorin, and simvastatin. These patients were randomly assigned to three groups, i.e., Group 1 (n=59), Group 2 (n=63), and Group 3 (n=59). Patients in Group 1, Group 2, and Group 3 were orally administered for 12 weeks (twice a day) with a placebo; soft chews providing (per day) 500 mg quercetin, 500 mg Vitamin C, 20 mg Vitamin B3, and 400 mcg folic acid; and soft chews providing (per day) 1000 mg quercetin, 1000 mg Vitamin C, 40 mg Vitamin B3, and 800 mcg folic acid, respectively. Both the serum total cholesterol levels and the serum LDL cholesterol levels were examined before and after treatment. As shown in Table 1 below, the combination of the statin and the soft chews significantly reduced serum total cholesterol levels in the patients treated thereby, as compared to the patients treated with the placebo.

TABLE 1

Serum Cholesterol Levels Before and After Treatment

| Serum Total Cholesterol (mg/dl) | Group 1 (n = 59) | Group 2* (n = 63) | Group 3** (n = 59) |
| --- | --- | --- | --- |
| Before Treatment | 206.9 | 206.7 | 209.6 |
| After Treatment | 205.3 | 197 | 192.7 |

*P = 0.046
**P ≤ 0.001

Changes of serum total and LDL cholesterol levels in the treated patients are shown in Table 2 below.

TABLE 2

Changes of Serum Total and LDL Cholesterol Levels Before and After Treatment

| | Group 1 (n = 59) | Group 2 (n = 63) | Group 3 (n = 59) |
| --- | --- | --- | --- |
| Changes of Total Serum Cholesterol (mg/dl) | −1.54 | −9.7$^a$ | −16.8$^c$ |
| Changes of Serum LDL Cholesterol (mg/dl) | −1.32 | −4.86$^b$ | −9.54$^c$ |

$^a$P = 0.046
$^b$P = 0.282
$^c$p ≤ 0.001

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of lowering the plasma cholesterol level of a subject, comprising administering to a subject in need thereof an effective amount of a first composition containing quercetin, resveratrol, vitamin C, and vitamin B3, and an effective amount of a second composition containing a statin, wherein the first composition has a weight ratio of 1:0.2-2.5:0.02-1 between quercetin, vitamin C, and vitamin B3.

2. The method of claim 1, wherein the weight ratio is 1:0.5-1:0.02-0.2.

3. The method of claim 1, wherein the weight ratio is 1:0.5-1:0.25-1.

4. The method of claim 2, wherein the weight ratio is 1:1:0.04.

5. The method of claim 1, wherein the effective amount of the first composition is an amount that provides 500 mg-1000 mg quercetin per day.

6. The method of claim 5, wherein the effective amount of the first composition is an amount that provides 500 mg quercetin per day.

7. The method of claim 5, wherein the effective amount of the first composition is an amount that provides 1000 mg quercetin per day.

8. The method of claim 1, wherein the statin is atorvastatin, cerivastatin, fluvastatin, mevastatin, pitavastatin, lovastatin, provastatin, rosuvastatin, or simvastatin.

9. The method of claim 8, wherein the statin is atorvastatin.

10. The method of claim 9, wherein the effective amount of the second composition is an amount that provides atorvastatin at 10-20 mg per day.

11. The method of claim 1, wherein the first composition further contains folic acid.

12. The method of claim 11, wherein the first composition has a weight ratio of 1:0.2-2.5:0.02-1:0.2-2 (mg/mg/mg/mcg) between quercetin, vitamin C, vitamin B3, and folic acid.

13. The method of claim 12, wherein the weight ratio is 1:0.5-1:0.02-0.2:0.5-1 (mg/mg/mg/mcg).

14. The method of claim 12, wherein the weight ratio is 1:0.5-1:0.25-1:0.5-1 (mg/mg/mg/mcg).

15. The method of claim 13, wherein the weight ratio is 1:1:0.04:0.8 (mg/mg/mg/mcg).

16. The method of claim 11, wherein the effective amount of the first composition is an amount that provides 500-1000 mg quercetin 10-1000 mg resveratrol, 500-1000 mg vitamin C, 20-40 mg vitamin B3, and 400-800 mcg folic acid per day.

17. The method of claim 16, wherein the effective amount of the first composition is an amount that provides 500 mg quercetin 10 mg resveratrol, 500 mg vitamin C, 20 mg vitamin B3, and 400 mcg folic acid per day.

18. The method of claim 16, wherein the effective amount of the first composition is an amount that provides 1000 mg quercetin, 1000 mg vitamin C, 40 mg vitamin B3, and 800 mcg folic acid.

19. The method of claim 11, wherein the statin is atorvastatin, cerivastatin, fluvastatin, mevastatin, pitavastatin, lovastatin, provastatin, rosuvastatin, or simvastatin.

20. The method of claim 19, wherein the statin is atorvastatin.

21. The method of claim 20, wherein the effective amount of the second composition is an amount that provides atorvastatin at 10-20 mg per day.

22. The method of claim 1, wherein the second composition further contains ezetimibe, colesevelam, fenofibrate, red rice yeast, or omega-3.

23. The method of claim 1, wherein the statin is simvastatin and the second composition further contains ezetimibe.

24. The method of claim 23, wherein the effective amount of the second composition is an amount that provides 10-80 mg simvastatin and ezetimibe in combination.

25. The method of claim 1, wherein the statin is provastatin and the second composition further contains fenofibrate.

26. The method of claim 25, wherein the effective amount of the second composition is an amount that provides 40 mg provastatin and 145 mg fenofibrate per day.

27. The method of claim 1, wherein the statin is atorvastatin and the second composition further contains colesevelam, fenofibrate, and ezetimibe.

28. The method of claim 1, wherein the statin is simvastatin and the second composition further contains ezetimibe.

29. The method of claim 28, wherein the effective amount of the second composition is an amount that provides 10-40 mg simvastatin and ezetimibe in combination and 1000 mg vitamin B3 per day.

30. The method of claim 1, wherein the statin is simvastatin and the second composition contains ezetimibe, and omega-3.

31. The method of claim 1, wherein the first composition is in dry form.

32. The method of claim 1, wherein the first composition is in liquid form.

33. The method of claim 1, wherein the first composition is a food product.

34. The method of claim 33, wherein the food product is tea, juice, milk, coffee, a soft drink, jelly, ice cream, yogurt, cereal, chocolate, a cookie, or a snack bar.

35. The method of claim 1, wherein the first composition is a dietary supplement.

36. The method of claim 35, wherein the first composition is in the form of a tablet, a capsule, a soft chew, or a gel.

37. The method of claim 11, wherein the second composition further contains ezetimibe, colesevelam, fenofibrate, red rice yeast, or omega-3.

* * * * *